(12) United States Patent  (10) Patent No.: US 6,585,680 B2
Bugge  (45) Date of Patent: Jul. 1, 2003

(54) SUCTION TUBE FOR SURGICAL PURPOSES

(75) Inventor: Mogens Bugge, Gothenburg (SE)

(73) Assignee: Scan-Mark, Inc., Minneapolis, MN (US)

(*) Notice: Subject to any disclaimer, the term of this patent is extended or adjusted under 35 U.S.C. 154(b) by 0 days.

(21) Appl. No.: 09/725,139

(22) Filed: Nov. 29, 2000

(65) Prior Publication Data

US 2001/0002432 A1 May 31, 2001

(51) Int. Cl.[7] ................................................ A61M 1/00
(52) U.S. Cl. ...................................................... 604/27
(58) Field of Search .................. 128/350; 604/35; 600/27

(56) References Cited

U.S. PATENT DOCUMENTS

| 4,317,452 A | * | 3/1982 | Russo et al. ............... 128/350 |
| 4,867,747 A | | 9/1989 | Yarger et al. |
| 5,024,615 A | | 6/1991 | Büchel |
| 5,505,710 A | | 4/1996 | Dorsey, III |
| 5,573,504 A | * | 11/1996 | Dorsey, III ................... 604/35 |
| 5,817,050 A | | 10/1998 | Klein |
| 5,827,218 A | | 10/1998 | Nguyen et al. |

FOREIGN PATENT DOCUMENTS

| DE | 2542509 | 4/1976 |
| DE | 4437834 | 4/1996 |
| DE | 4103972 | 8/1996 |
| DE | 19535349 | 3/1997 |
| DE | 19638058 | 3/1997 |

* cited by examiner

Primary Examiner—Henry Bennett
Assistant Examiner—Sabrina Dagostino
(74) Attorney, Agent, or Firm—Ostrolenk, Faber, Gerb & Soffen, LLP

(57) ABSTRACT

Suction tube for surgical purposes, especially for draining of body compartments in connection to an organ, which suction tube comprise an inner tube, whose distal end is open and a outer tube, provided with a peripherally arranged holes, wherein the outer tube exhibits a cross section having at least one essentially flat side, being faced against the organ during draining.

5 Claims, 4 Drawing Sheets

SUCTION TUBE FOR SURGICAL PURPOSES

The present invention relates to a suction tube for surgical purposes, especially for draining of body compartments in connection to an organ, which suction tube comprises an inner tube, whose distal end is open, and an outer tube, being provided with peripherally arranged holes.

Suction tubes are used in surgery when undesired fluids is to be removed. By means of a suction tube, connected to a vacuum pump, a fluid may even be sucked away from difficult locations. Above all, it is necessary in the heart and lung surgery to suck fluids behind the heart or the lungs, respectively, without harming the tissue.

Known suction tubes comprise an inner tube and an outer tube, said outer tube being perforated, whilst the inner tube only has an orifice opening at the tree end. The suction tube may be bent, as to be able to be brought behind the organ in question.

Known devices of this kind have the disadvantage that the edges of the holes on the outer tube may harm the tissue or even the organ, e.g., the heart, the lungs, the pleura, the liver, etc., during the insertion or at withdrawal of the suction tube. When it concerns the heart, the abrasion caused by the suction tube may cause heart arrhythmia, which may lead to heart fibrillation.

The object of the invention is to provide a suction tube, which is even insertable in narrow passages, that has a good suction capacity and is gentle to the tissue. This object is being solved in that the outer tube exhibits a cross section, having at least one essentially flat side, which is faced against the organ during draining.

BRIEF DESCRIPTION OF THE DRAWINGS

The invention will hereafter be closer described by means of embodiments on the enclosed drawings.

FIG. 4 shows the cross section along the line IV—IV in FIG. 1 of the suction tube according to the invention, FIG. 4a shows a variation of FIG. 4 in which the flat side of the outer tube is not perforated.

FIG. 4b shows a variation of FIG. 4 in which only the flat side of the outer tube is perforated.

DESCRIPTION OF THE EMBODIMENTS

Figure 1:
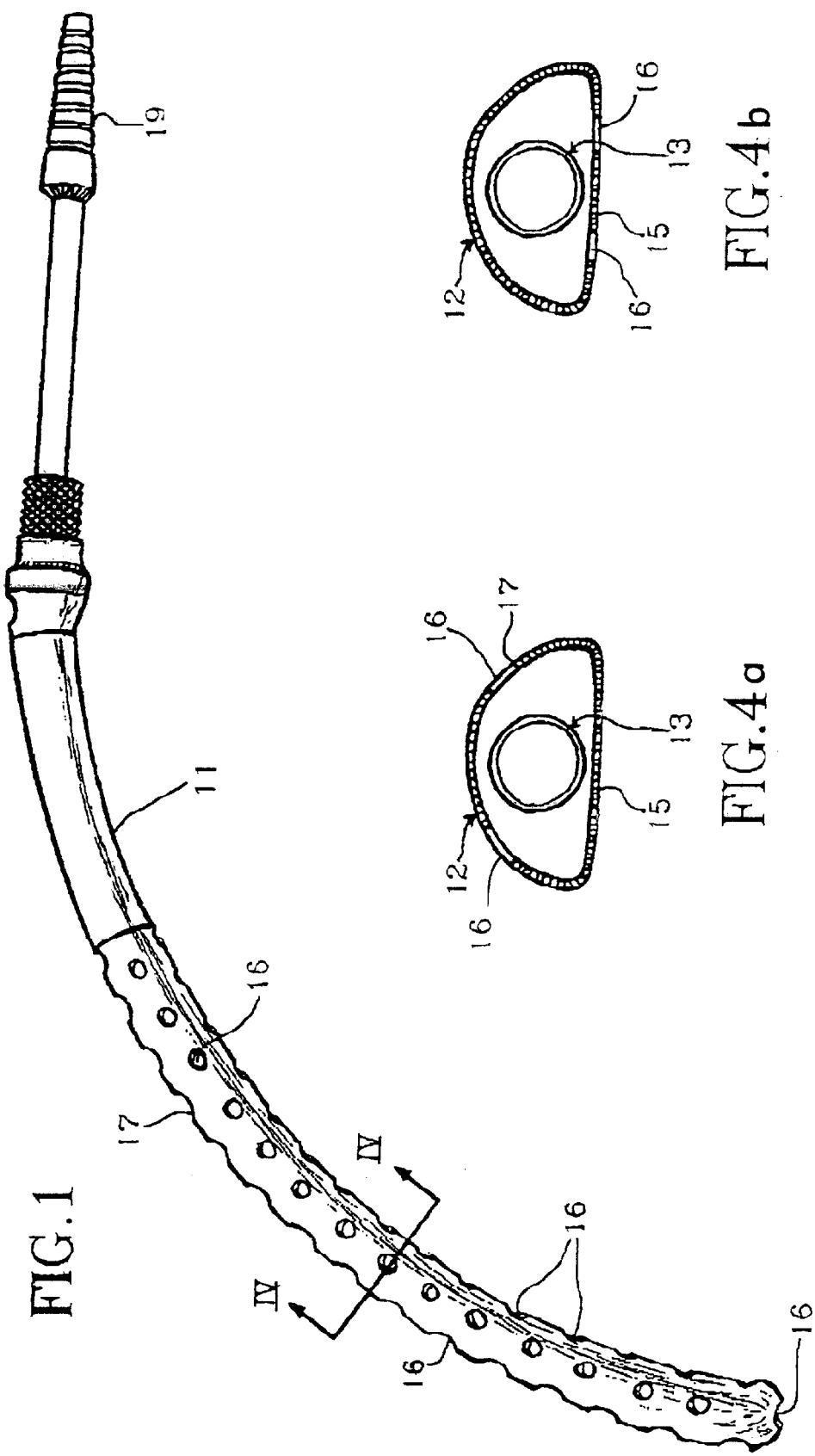
FIG. 1 shows a view from above of one embodiment of the suction tube according to the invention.
Figure 2:
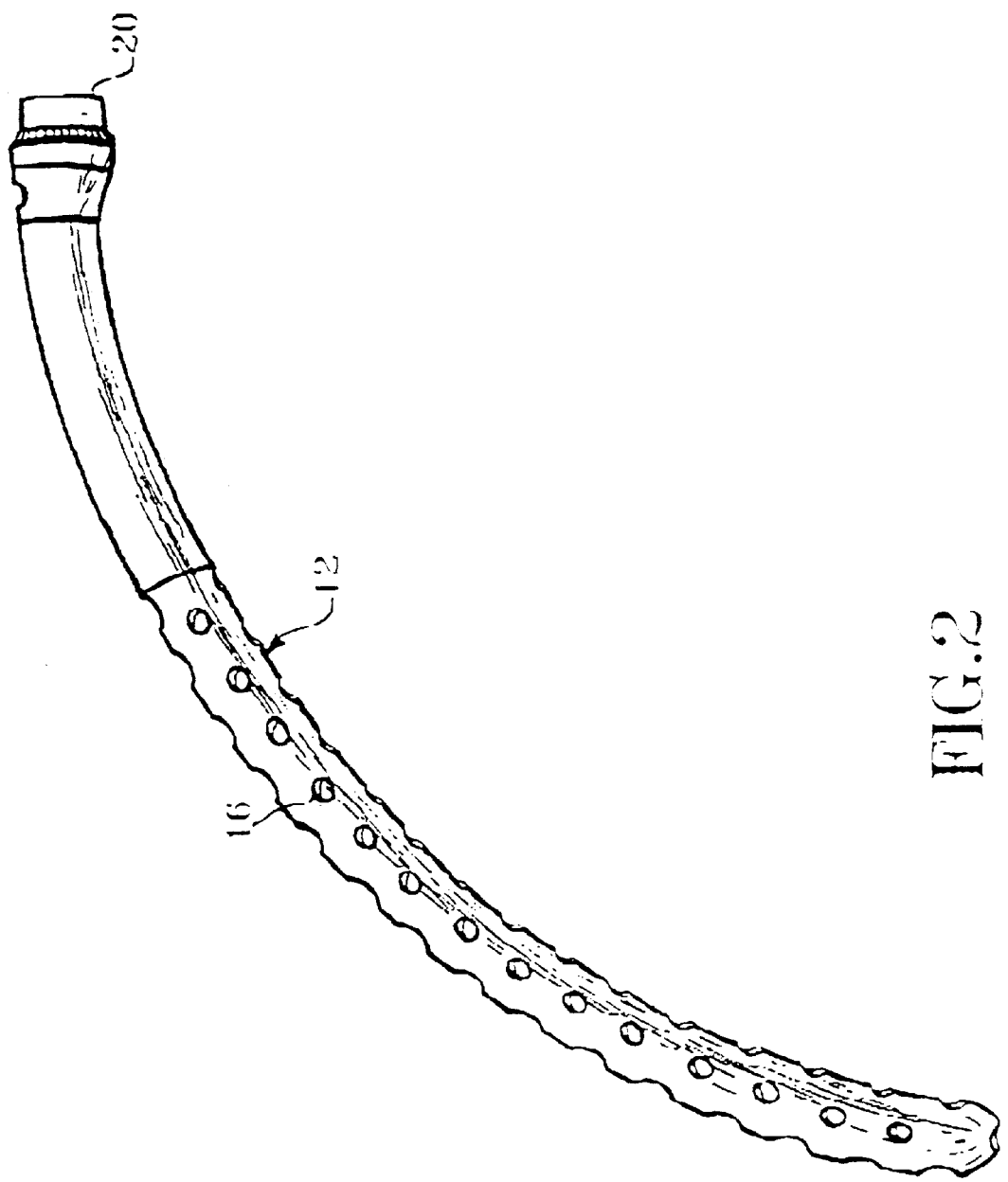
FIG. 2 shows the outer tube of the suction tube according to the invention.
Figure 3:
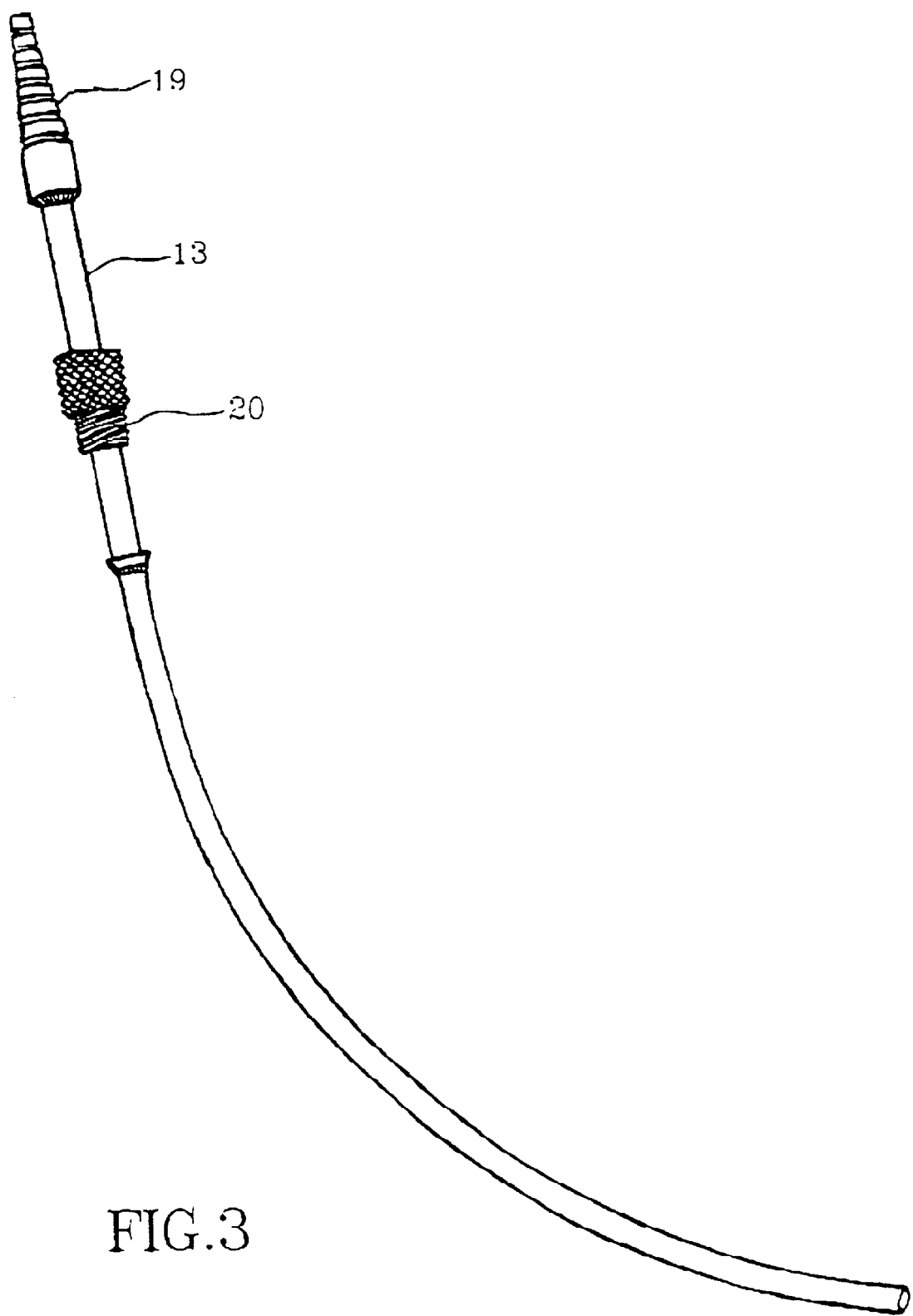
FIG. 3 shows the inner tube of the suction tube according to the invention.
Figure 5:
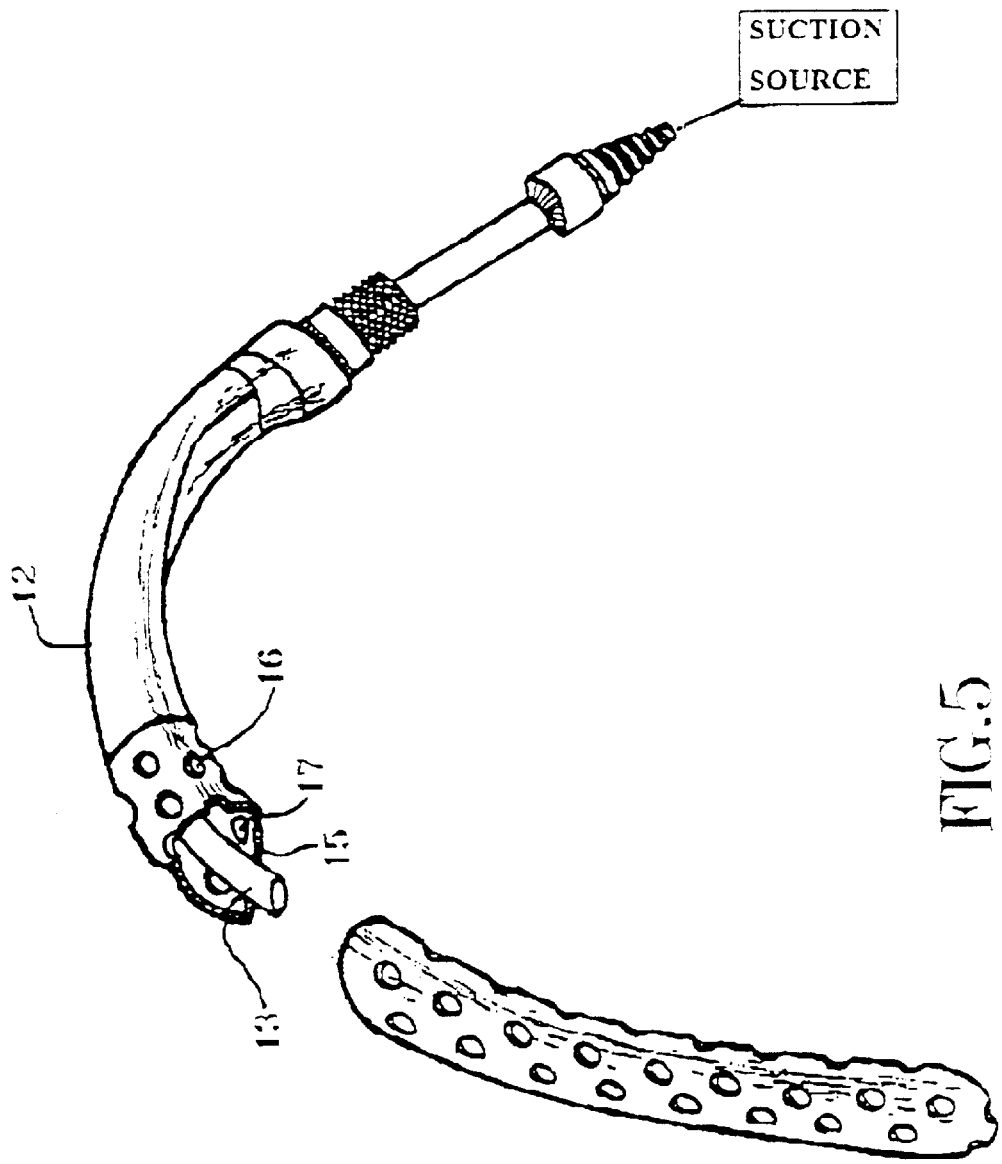
FIG. 5 shows a perspective view of the suction tube according to the invention in assembled state.

In FIG. 1, 11 denotes a schematically representation of a bent suction tube, to be inserted in narrow compartments, especially behind an organ. The suction tube 11 comprise an outer tube 12, represented in FIG. 2, and a inner tube 13, represented in FIG. 3. The outer tube 12, is provided with peripherally arranged holes 16 and is arranged with a flat side 15 of the cross section 14, which likewise can exhibit holes 16. The flat side 15 makes the edges 17 of the holes 16 less sharp and prevents thereby totally or to a certain extent damage of the tissue.

In the embodiment represented in FIG. 1, the cross section 14 of the outer tube 12 has a half-rounded shape, which is being illustrated in FIG. 4. The cross section 14 may also have other shapes, e.g., essentially triangular, whereby the corners are softly rounded. The inner tube 13 is open at its distal end, as to be able to suck the fluid through the holes 16 of the outer tube 12.

A variant construction of outer tube 12 is shown in FIG. 4a, in which there are no holes in flat side 15. FIG. 4b shows another variant in which only flat side 15 has holes. The outer tube 12 is provided with internal threads 20, so that it may be screwed on the inner tube 13, whereby the suction tube 11 according to the invention is formed. The suction tube 11 exhibits an end portion 19, that may be connected to a suction source.

The invention also includes a method for using a suction tube in connection to an organ, especially in the heart and/or lung surgery, said suction tube comprising an inner tube, whose distal end is open and an outer tube connected to the inner tube, provided with peripherally arranged holes, wherein the outer tube exhibits a cross section having at least one essentially flat side, being faced against the organ during draining for surgical purposes, comprising the steps of:

inserting the distal end of said suction tube behind the organ in question;

connecting said suction tube to a suction source; and draining the body compartments from fluids adjacent to said organ.

What is claimed is:

1. A suction device for draining a body cavity comprising:
   a perforated outer tube; and
   an inner tube disposed within the outer tube,
   the inner tube being open at a first distal end thereof, and connectable at a second opposite end to a source of suction,
   the outer tube having a cross-section including at least one substantially flat surface adapted to rest against an organ within the body cavity.

2. A suction device according to claim 1, wherein the cross-section of the outer tube includes a curved surface disposed in opposition to the flat surface.

3. A suction device according to claim 1, wherein the cross section of the outer tube is substantially triangular, with softly rounded corners.

4. A suction device according to claim 1, wherein the flat surface of the outer tube is unperforated.

5. A suction device according to claim 1, wherein only the flat surface of the outer tube is perforated.

* * * * *